us006982322B1

United States Patent
Ikeda et al.

(10) Patent No.: US 6,982,322 B1
(45) Date of Patent: Jan. 3, 2006

(54) MONOCLONAL ANTIBODIES AGAINST HUMAN APOPTOSIS INHIBITORY PROTEIN NAIP AND METHOD FOR ASSAYING NAIP

(75) Inventors: Johe Ikeda, Tokyo (JP); Harumi Sakai, Kanagawa (JP)

(73) Assignees: Japan Sciences and Technology Corporation, Saitama (JP); Toyo Boseki Kabushiki Kaisya, Osaka (JP)

( * ) Notice: Subject to any disclaimer, the term of this patent is extended or adjusted under 35 U.S.C. 154(b) by 0 days.

(21) Appl. No.: 09/830,338

(22) PCT Filed: Oct. 22, 1999

(86) PCT No.: PCT/JP99/05841

§ 371 (c)(1),
(2), (4) Date: Jul. 11, 2001

(87) PCT Pub. No.: WO00/24889

PCT Pub. Date: May 4, 2000

(30) Foreign Application Priority Data

Oct. 26, 1998   (JP)   ................................. 10/304550

(51) Int. Cl.
*C07K 16/00* (2006.01)
(52) U.S. Cl. .................. 530/388.1; 530/387.1
(58) Field of Classification Search ............. 530/387.1, 530/388.1, 388.15
See application file for complete search history.

(56) References Cited

U.S. PATENT DOCUMENTS 6,511,828 B1 * 1/2003 Thompson et al. ........ 435/69.2

FOREIGN PATENT DOCUMENTS

WO    97/26331    7/1997

OTHER PUBLICATIONS

Harlow et al (1988, Antibodies A Laboratory Manual, Cold Spring Harbor Laboratory, pp. 556, 588, 579-81 only).*
Roy et al (Dec. 1, 1997, EMBO J., vol. 16, pp. 6914-25).*
Biological Abstracts, No. 199799598887, D. G. Xu et al., "Distribution of Neuronal Apoptosis Inhibitory Protein-Like Immunoreactivity in the Rat Central Nervous System", & Journal of Comparative Neurology, 1997, vol. 382, No. 2, pp. 247-259.
Natalle Roy et al., "The Gene for Neuronal Apoptosis Inhibitory Protein is Partially Deleted in Individuals with Spinal Muscular Atrophy", Cell, 1995, vol. 80, No. 1, pp. 167-178.

* cited by examiner

*Primary Examiner*—Jeffrey Siew
*Assistant Examiner*—Misook Yu
(74) *Attorney, Agent, or Firm*—Wenderoth, Lind & Ponack, L.L.P.

(57) ABSTRACT

An anti-NAIP monoclonal antibody recognizing a human apoptosis inhibitory protein NAIP having the amino acid sequence of SEQ ID NO: 1, which is produced from hybridoma prepared by fusing a myeloma cell line with antibody-producing cell of mammal immunized by antigen containing a polypeptide which comprises amino acid sequence of the 256–586th, the 841–1052nd or parts thereof in SEQ ID NO: 1, NAIP assay method using the antibody, and NAIP assay kits.

9 Claims, 2 Drawing Sheets

MONOCLONAL ANTIBODIES AGAINST HUMAN APOPTOSIS INHIBITORY PROTEIN NAIP AND METHOD FOR ASSAYING NAIP

This application is a 371 of PCT/JP99/05841, filed Oct. 22, 1999.

TECHNICAL FIELD

The present invention relates to monoclonal antibodies, which specifically recognize Human Apoptosis Inhibitory Protein NAIP and an immunoassay method of the NAIP.

BACKGROUND ART

Apoptosis is a type of programmed death of a cell, in which phenomena such as lack of contact with the surrounding cells, inspissation of cytoplasm, aggregation of chromatin and karyopyknosis related to the activity of endonuclease, fragmentation of nucleus, the cell being changed into membrane-wrapped bulboid corpuscles, englobement of the bulboid corpuscles by the adjacent macrophage or epithelial cells, or fragmentation of the nucleosome unit of DNA into DNA fragments of 180–200 base length by the activity of endonuclease are observed. Apoptosis has been discussed as a mechanism in which the final fragments of apoptic somatic cells exhibiting the aforementioned phenomena are englobed by the adjacent cells (e.g., "Immunology Today", 7: 115–119. 1986: Science 245: 301–305. 1989).

As the gene that controls the apoptosis described above, the bcl-2 gene, which is one of oncogene discovered from B cell lymphoma in 1985, is known. This bcl-2 gene appears quite frequently in cells of the immune system or neuronal cells. It is assumed that the substance produced as a result of expression of the gene suppresses the apoptosis of such cells, whereby the function of the human immune and neuronal systems are constantly maintained the homeostasis thereof. In addition, as the bcl-2 gene appears in a fetus in an especially wide range, it is assumed that the gene plays an important role in morphogeny during the ontogenic process.

On the other hand, the inventors of the present application have isolated Neuronal Apoptosis Inhibitory Protein (NAIP) gene, as the gene causing Spinal Muscular Atrophy (SMA) which is a familial genetic disease, from the human chromosome 5q13.1 domain (Roy et al., Cell 80: 167–178, 1995), and they have filed a patent application for the gene (PCT/CA95/00581). Specifically, it is considered that the mutation of the NAIP gene or the decrease in the number of copies therefrom causes apoptosis of spinal neurons, resulting in the development of SMA. Further, in a case in which the NAIP gene is introduced into various cultured cells and stimulation is provided to the cells to induce apoptosis, it has been found out that the death of the cells is significantly prevented (Liston et al., "Nature" 379: 349–353, 1996). In this case, it has also been found out that NAIP functions as the apoptosis inhibitory factor not only to the neuronal cells but also to the somatic cells as a whole.

The inventors of the present application have isolated the full amino acid sequence of NAIP and cDNA encoding the NAIP, and filed a patent application thereof (Japanese Patent Application No. 9-280831).

As described above, NAIP is a protein which is concerned with various apoptosis-related diseases including SMA. In order to understand the mechanism of a patient's developing such diseases, diagnose the risk for developing the diseases, prevent the development of the diseases or reduce the severity of the diseases, and develop the medical technique and medicines for treatment, it is essential to accurately assay the amount of expressed NAIP.

The inventions of the present application has been contrived in consideration of the aforementioned task, and objects of the present invention is to provide anti-NAIP monoclonal antibodies, which are essential for assaying NAIP and a NAIP assaying method using the monoclonal antibodies.

DISCLOSURE OF INVENTION

The inventors of the present application have assiduously studied the solution of the aforementioned task, and as a result, discovered that the epitopes of NAIP exist in the amino acids of the 256–586th and the 841–1052nd in SEQ ID NO: 1.

The present application, on the basis of the discovery, provides an anti-NAIP monoclonal antibody recognizing a human apoptosis inhibitory protein NAIP having the amino acid sequence of SEQ ID NO: 1, which is produced from hybridoma prepared by fusing a myeloma cell line with antibody-producing cell of mammal immunized by antigen containing a polypeptide which comprises amino acid sequence of the 256–586th, the 841–1052nd or parts thereof in SEQ ID NO:1.

The present application provides, as specific embodiments of the monoclonal antibody: anti-NAIP monoclonal antibody hnmc365, which is produced from hybridoma 656-1 (FERM BP-6919), and its epitope is the 354–365th region in SEQ ID NO: 1; anti-NAIP monoclonal antibody hnmc381, which is produced from hybridoma 656-2 (FERM BP-6920), and its epitope is the 373–387th region in SEQ ID NO: 1; and anti-NAIP monoclonal antibody hnmc841, which is produced from hybridoma 841 (FERM BP-6921), and its epitope is the 841–1052nd region in SEQ ID NO: 1. Each hybridoma was deposited on Oct. 19, 1999 with the National Institute of Bioscience and Human-Technology. Agency of Industrial Science and Technology, 1–3, Higashi 1-chome, Tsukuba-shi, Ibaraki-ken, 305–8566, Japan.

The present application provides the first method of assaying NAIP, which comprises contacting a marker-labeled anti-NAIP monoclonal antibody with a sample containing NAIP thereby binding the marker-labeled antibody with NAIP, and measuring signal strength of the marker in the bound structure.

In the first assay method, it is preferred that the anti-NAIP monoclonal antibody is any one of said hnmc365, hmnc381 and hmnc841, and that the marker is an enzyme, a radioactive isotope or a fluorescent colorant.

The present application provides the second method of assaying NAIP which comprises contacting an anti-NAIP primary antibody with a sample containing NAIP thereby binding the primary antibody with NAIP, further binding the bound structure with an anti-NAIP secondary antibody, and measuring signal strength of a marker bound with the secondary antibody, wherein:

(1) the primary antibody and the secondary antibody are both said anti-NAIP monoclonal antibody;
(2) the primary antibody is said anti-NAIP monoclonal antibody and the secondary antibody is an anti-NAIP polyclonal antibody; or
(3) the primary antibody is an anti-NAIP polyclonal antibody and the secondary antibody is said anti-NAIP monoclonal antibody.

In the second assay method, it is preferred that the primary antibody is immobilized on solid phase, that the anti-NAIP monoclonal antibody is any one of said hnmc365, hmnc381 and hmnc841, and that the marker is an enzyme, a radioactive isotope or a fluorescent colorant.

The present application provides the first kit for assaying NAIP at least including:
(a) a plate on which an anti-NAIP primary antibody is immobilized; and
(b) an anti-NAIP secondary antibody labeled with a marker, wherein:
  (1) the primary antibody and the secondary antibody are both said anti-NAIP monoclonal antibody;
  (2) the primary antibody is said anti-NAIP monoclonal antibody and the secondary antibody is an anti-NAIP polyclonal antibody; or
  (3) the primary antibody is an anti-NAIP polyclonal antibody and the secondary antibody is said anti-NAIP monoclonal antibody.

In the first assay kit, it is preferred that the marker is a radioactive isotope, a fluorescent colorant or an enzyme, and in the case of the marker being emzyme the kit further includes:
(c) a substrate which develops a color by the enzyme activity.

The present invention provides the second kit for assaying NAIP at least including:
(a) a plate on which an anti-NAIP primary antibody is immobilized;
(b) an anti-NAIP secondary antibody; and
(c) a marker to be bound with the secondary antibody, wherein:
  (1) the primary antibody and the secondary antibody are both said anti-NAIP monoclonal antibody;
  (2) the primary antibody is said anti-NAIP monoclonal antibody and the secondary antibody is an anti-NAIP polyclonal antibody; or
  (3) the primary antibody is an anti-NAIP polyclonal antibody and the secondary antibody is said anti-NAIP monoclonal antibody.

In the second assay kit, it is preferred that the marker is a radioactive isotope, a fluorescent colorant or an enzyme, and in the case of the marker being emzyme the kit further includes:
(c) a substrate which develops a color by the enzyme activity.

In said assay kits, it is further preferred that the anti-NAIP monoclonal antibody is any one of said hnmc365, hmnc381 and hmnc841.

BEST MODE FOR CARRYING OUT THE INVENTION

The anti-NAIP monoclonal antibodies of the present invention may be produced by the following steps, for example, according to the known method ("Monoclonal Antibody" Takaaki NAGAMUNE and Hiroshi TERADA, Hirokawa Shoten, 1990; "Monoclonal Antibody" James W. Goding, third edition, Academic Press, 1996).

1. Preparation of Hybridomas

A mammal animal is immunized by using an immunogen containing a polypeptide, the polypeptide comprising amino acid sequence of the 256–586th, the 841–1052nd or parts thereof in SEQ ID NO: 1. An additional immunization is optionally carried out according to necessity so that the animal is sufficiently immunized. Next, the antibody-producing cells (lymphatic cells or spleen cells) are isolated from the animals and fused cells are obtained by fusing the antibody-producing cells and myeloma cells. A plurality of cells that respectively produce the targeted monoclonal antibody are selected and cultured, thereby obtaining hybridomas. The steps for the procedure will be each described in detail hereinafter.

a) Preparation of Immunogen

The polypeptide having the amino acid sequence of the 265–586th in SEQ ID NO: 1 may be prepared by, for example, cleaving NAIP cDNA having the nucleotide sequence of SEQ ID NO: 2 with a restriction enzyme to obtain a DNA fragment containing the nucleotide sequence of the 1056–2049th, and expressing the DNA fragment in an appropriate host-vector system. The polypeptide having the amino acid sequence of the 841–1052th in SEQ ID NO: 1 may be prepared by expressing a DNA fragment having the nucleotide sequence of the 2812–3447th in SEQ ID NO: 2 in an appropriate host-vector system.

Alternatively, polypeptide having a partial sequence (10–20 amino acids) of the amino acids sequence of the 256–586th or the 841–1052nd region in SEQ ID NO: 1 may be prepared. In this case, by using polypeptides of different sequences, hybridomas each producing monoclonal antibody of different epitope can be obtained.

These polypeptides may be also used in a form of a fusion protein in which the polypeptide is fused with other proteins (e.g., glutation-S-transferase: GST). Use of such fusion proteins is especially preferable in terms of facilitating and ensuring the separation process of the targeted protein from the expressed product of the host-vector system and the screening process (described below) of the hybridoma.

It should be noted that the polypeptide may be that having amino acid sequence in which at least one amino acid residue is deleted or substituted or added in amino acid sequence of the 256–586 or a part in SEQ ID NO: 1.

b) Immunization of Animals

As the animals to be immunized, mammals used in the known hybridoma preparation methods can be employed. Specific examples of the animals include mice, rats, goats, sheep, cows and horses. However, in terms of availability of myloma cells to be fused with the isolated tibody-producing cells, it is preferable to use mice or rats as the animals to be immunized. There is no particular restriction on the strains of mice and rats actually used. In the case of mice, examples of strains thereof which can be used include A, AKR, BALB/c, BDP, BA, CE, C3H, 57BL, C57BR, C57L, DBA, FL, HTH, HT1, LP, NZB, NZW, RF, RIII, SJL, SWR, WB, 129. In the case of rats, examples of strains thereof that can be used include Low, Lewis, Spraque, Daweley, ACI, BN, Fisher. Among them, if the suitability in being fused with the myeloma cells described below is considered, the "BALB/c" strain of mice and the "Low" strain of rats are especially preferable as the animals to be immunized. It is preferable that the mouse or rat is 5–12 week old when it is immunized.

The immunization of the animal can be carried out by subcutaneously or intraperitoneally dozing the polypeptide solution as an immunogen, into the animal. The dosing schedule of the antigen varies depending on the types of the subject animal or the differences between the individual animals. In general, the antigen is preferably dosed totally 2–6 times with 1–2 weeks of the interval between doses. The amount of the antigen to be dosed also varies depending on the types of the animal and the differences between the individual animals. In general, the amount of the antigen to be dosed is approximately 10–100 $\mu g/\mu l$.

c) Fusion of Cells

1–5 days after the final immunization in the aforementioned dosing schedule, spleen cells or lymphatic cells containing the antibody-producing cells are sterilely collected from the immunized animal. The separation of the antibody-producing cells from the spleen cells or the lymphatic cells can be carried out according to the known methods.

Next, the antibody-producing cells are fused with myeloma cells. There is no particular restriction on the myeloma cells to be used, and those appropriately selected from the known cell lines may be used. However, in consideration of the convenience at the time of selecting hybridomas from the fused cells, it is preferable to employ a HGPRT (Hpoxanthine-guanine phosphoribosyl transferase) defective line for which a selection procedure has been established. Specific examples thereof include: X63-Ag8(X63), NS1-Ag4/1 (NS-1), P3X63-Ag8.UI(P3UI), X63-Ag8.653(X63.653), SP2/0-Ag14(SP2/0), MPC11-45.6TG1.7(45.6TG), FO, S149/5XXO.BU.1, which are derived from mice; 210.RSY3.Ag.1.2.3(Y3) derived from rats; and U266AR(SKO-007), GM1500.GTG-A12 (GM1500), UC729-6, LICR-LOW-HMy 2(HMy2), 8226AR/NIP4-1(NP41), which are derived from human.

The antibody-producing cells may be fused with the myeloma cells in an appropriate manner, according to the known method, under a condition in which the survival rate of the cells does not drop to such an extremely low level. Examples of such methods include a chemical method in which the antigen-producing cells are mixed with the myeloma cells in a polymer (e.g., polyethylene glycol) solution of a high concentration, a physical method in which electric stimulation is utilized, and the like.

The selection of the fused cells from the non-fused cells is preferably carried out according to the known HAT (Hpoxanthine/Aminopterin/Thymidine) selection method. This method is effective when fused cells are obtained by using myeloma cells of a HGPRT defective line that is not viable under the presence of aminopterin. That is, by cultivating fused cells and cells which have not been fused in a HAT culture, only the fused cells that is resistant to aminopterin are selectively remained and allowed to reproduce.

d) Screening of Hybridoma

The screening of the hybridoma which produce the targeted monoclonal antibody can be performed by the known EIA (Enzyme Immunoassay), RIA (Radio Immunoassay), fluorescent antibody methods and the like. When a fused protein is employed as the immunogen, the hybridoma can be screened more reliably by carrying out the aforementioned screening methods for the protein which is the partner of the fusion, as well.

By conducting such a screening process, hybridomas respectively producing monoclonal antibodies having different epitope domains are obtained. Accordingly, the monoclonal antibodies of the present invention include all of the plural types of monoclonal antibodies respectively produced by the hybridomas prepared by the method described above.

After the screening process, the hybridomas are then subjected to cloning by the known methods such as the methylcellulose method, the soft agarose method and the limiting dilution method, so that the hybridomas can be used for producing the antibodies.

The hybridomas obtained by the aforementioned method can be stored in the frozen state in liquid nitrogen or in a freezer in which the temperature is no higher than −80° C.

2. Production of the Monoclonal Antibodies and Purification Thereof

The monoclonal antibodies that specifically recognize NAIP can be obtained by cultivating, according to the known method, the hybridomas prepared as described in the paragraph 1 above.

The cultivation may be conducted, for example, in the culture having the same composition as that used in the cloning method described above. Alternatively, in order to produce a large amount of the monoclonal antibodies, it is acceptable to inject the hybridoma intraperitoneally to a mouse and collect the monoclonal antibody from the ascites of the animal.

The monoclonal antibody obtained in such a manner can be purified by the methods including the ammonium sulfate salting out method, the gel filtration method, the ion-exchange chromatography method, the affinity chromatography method and the like.

Next, the NAIP assay method of the present invention will be described hereinafter.

In the first assay method, a solution of the marker-labeled anti-NAIP monoclonal antibody (M-mAb) is contacted with a sample containing NAIP so that the marker-labeled monoclonal antibody is bound with NAIP, and the bound structure (M-mAb: NAIP) are separated. As the means for separation, any known methods including the chromatography method, the salting out method, the alcohol precipitation method, the enzyme method, the solid phase method and the like may be employed. In a case in which an enzyme is used as the marker, a substrate that develops a color as a result of decomposition by the enzyme activity is added. In this case, the activity of the enzyme is measured by optically measuring the amount of the decomposed substrate and the activity of the enzyme is converted into the amount of bound antibody, so that the amount of NAIP is calculated on the basis of the comparison of the obtained amount of bound antibody with the reference value. In a case in which a radioactive isotope is used as the marker, the amount of the radioactive rays emitted from the radioactive isotope is measured by a scintillation counter or the like. In a case in which a fluorescent colorant is used as the marker, a device in which a fluorescent microscope is incorporated can measure the magnitude of fluorescence.

In the second assay method, two types of antibodies whose epitope domains for NAIP are different from each other (the primary antibody and the secondary antibody) are used. Specifically, at first the primary antibody (Ab I) is contacted with a sample containing NAIP so that the primary antibody and NAIP are bound with each other. The bound structure (Ab I: NAIP) is bound with the secondary antibody that has been marker-labeled (M-Ab II), and the signal strength of the marker in the bound structure of the three components (Ab I: NAIP: M-Ab II) is measured. Optionally, in order to make the signal stronger, it is acceptable to allow the bound structure (Ab I: NAIP) to be bound, at first, with secondary antibody that is not marker-labeled and then allow the secondary antibody to be bound with the marker. Such bonding of the secondary antibody with a marker-labeled molecular can be effected, for example, by using the secondary antibody with biotin and tha marker with avidin. Further, it is also acceptable that an antibody (the tertiary antibody) that recognizes a portion of the secondary antibody (e.g., Fc domain) is marker-labeled, so that the tertiary antibody is bound with the secondary antibody (II). The anti-NAIP monoclonal antibodies of the present invention may be used for both the primary antibody and the secondary antibody. Alternatively, the anti-NAIP polyclonal antibody (the anti-serum of the animals immunized by the aforementioned polypeptide, for example) may be used for one of the primary antibody and the secondary antibody.

Although this second method can be carried out either in the liquid phase or on the solid phase, it is preferable to carry out the method on the solid phase, in order to make the assay of extremely small amounts and the operation as a whole easier. More specifically, the solid phase method includes the steps of: providing the primary antibody on a resin plate or the like so that the primary antibody is immobilized; allowing the antibody on the solid state to be bound with NAIP; washing off the NAIP which is not bound to the antibody; allowing the bound NAIP remaining on the plate to be bound with the secondary antibody; and measuring the signal strength of the secondary antibody. This is what is called the "sandwich method", and widely used as "ELISA" (enzyme linked immunospecific assay) when an enzyme is used as the marker.

In the methods described above, there is no particular limitation on the enzyme used as the marker, as long as the turn over number of the enzyme is relatively large, the enzyme is stable after being bound with the antibody, the enzyme specifically acts on the substrate so that the substrate develops a color, and other required conditions are satisfied. Examples of the enzyme include the enzymes commonly used for EIA, such as peroxydase, β-galactosidase, alkaliphosphatase, glucoseoxydase, acetylchorine-esterase, glucose-6-phosphorylation dehydrogenase, malic acid dehydrogenase and the like. Further, enzyme inhibitors and coenzymes may also be used. Bonding of these enzymes with the monoclonal antibody can be carried out according to the known method which employs a cross-linking agent such as maleimide compounds. As the substrate, any suitable known compounds may be used, depending on the types of the enzyme that is actually used. In a case in which peroxydase is used as the enzyme, 3, 3' 5,5'-tetramethylbenzidine may be used as the substrate. In a case in which alkliphosphatase is used as the enzyme, para-nitrophenol or the like may be used as the substrate.

In a case in which a radioactive isotope is used as the marker, examples of the radioactive isotope include those used in the standard RIA process such as $^{125}I$ and $^{3}H$. Examples of the fluorescent colorants include those used in the standard fluorescent antibody method such as fluorescence isothiocyanate (FITC) or tetramethylrhodamine isothiocyanate (TRITC).

The assay kits of the present invention may be used for the "sandwich method" in which the aforementioned second assay method is carried out on the solid phase. Such kits of various types are commercially available in accordance with the types of the components to be assayed. The assay kits of the present invention may be basically constituted of various components used in known and commercially available kits, except that the aforementioned anti-NAIP monoclonal antibody and/or the anti-NAIP polyclonal antibody is used as the antibodies. In addition, the assay kits of the present invention including the components described above may be provided with a washing solution for washing off the NAIP which has not been bound and/or the secondary antibody which has not been bound.

EXAMPLES

The present invention will be described in detail by examples hereinafter. It should be noted, however, that the present invention is not limited to any of these examples.

Example 1

Production of the Monoclonal Antibodies (1) Preparation of the Immunogen

The 1056–2049th region of NAIP cDNA of which nucleotide sequence is shown in SEQ ID NO: 2 was amplified, and the DNA fragment (NAIP.256–586) was inserted at the EcoR I site of pGEX-3X (by Pharmacia Co.). After confirming the nucleotide sequence, the host *Escherichia coli* BL21 (DE3) pLysS was transformed by this recombinant vector pGEX-3X (NAIP.256–586) and cultivated in the LB medium for 5 hours at 30° C. Thereafter, IPTG was added to the medium and the cultivation was continued at 20° C. for 3 hours. The bacteria was separated by centrifuging, dissolved into the dissolving solution (PBS, Triton X-100), frozen at −80° C. and melted, and then subjected to ultrasonic destruction. The product was centrifuged at 1000× g for 30 minutes, the supernatant was introduced to a glutathione sepharose 4B column so as to pass through it, whereby fusion protein GST-NAIP(256–586) was obtained.

In addition, the 2812–3447th region of NAIP cDNA of which nucleotide sequence is shown in SEQ ID NO: 2 was amplified, and the DNA fragment (NAIP841–1052) was inserted at the BamHI-SalI site of pGEX-4X-3(by Pharmacia Co.). Thereafter, the same method as described above was repeated, thereby obtaining the fusion protein GST-NAIP(841–1052).

(2) Immunization of the Animal

50 μg/μl of each of the fusion proteins obtained in the aforementioned (1) was dosed to a Balb/c mouse, intraperitoneally, as the initial immunization. The second immunization was performed 2 weeks after the initial immunization, and immunization was conducted totally six times with one-week interval. At the initial immunication, the fusion protein was dosed in a state in which Freund complete adjuvant of the equal amount was mixed thereto. At the second to fifth immunization, the fusion protein was dosed in a state in which Freund incomplete adjuvant was mixed thereto. At the final immunization, only the fusion protein solution was dosed.

(3) Fusion of Cells

The spleen cells were sterilely isolated three days after the final immunization. The collected spleen cells and the myeloma cell line SP2/0-Ag14 derived from mice were mixed and then subjected to the fusing treatment by using polyethylene glycol #4000. The obtained cells were planted on a 96-hole plate, and the fused cells were selected by the HAT culture.

(4) Screening

An ELISA plate on which the NAIP polypeptide used as the immunogen was provided on the solid state and an ELISA plate on which GST was provided in the solid state were prepared. Clones that did not react to the GST plate but reacted only to the NAIP plate were selected and subjected to screening. Next, among the supernatants of the cultures of respective hybridomas, the wells reacted to the NAIP polypeptide were regarded as positive. The cloning of the hybridomas was carried out by using the positive wells in the limiting dilution method. The screening process was repeated for the cultures of the hybridomas that were supposed to have only single-type clones, whereby a plurality of hybridomas was obtained. Among these plural hybridomas, hybridomas 656-1, 656-2 and hnmc841 were deposited to National Institute of Bioscience and Human-Technology. The deposit Nos. of these hybridomas are FERM BP-6919 (hybridoma 656-1), FERM BP-6920 (hybridoma 656-2) and FERM BP-6921 (hybridoma hnmc841), respectively.

(5) Production of the Monoclonal Antibodies

Three types of the hybridomas obtained as described above were dosed to a Balb/c mice, intraperitoneally, and the ascites containing the monoclonal antibody was collected after one week. From the collected ascites, the three types of monclonal antibodies hnmc365, hnmc381 and hnmc841 were purified by using an affinity column in which protein G was used.

It was confirmed that the monoclonal antibody hnmc365, produced by hybridoma 656-1 which had been prepared by using fusion protein GST-NAIP( 256–586) as the immunogen, belongs to the subclass IgG1 and the epitope thereof is the amino acid sequence of the 254–368th region in SEQ ID NO: 1. It was also confirmed that the monoclonal antibody hnmc381 produced by hybridoma 656-2 belongs to the subclass IgG2b and the epitope thereof is the amino acid sequence of the 373–387th region in SEQ ID NO: 1. Further, it was confirmed that the monoclonal antibody hnmc841, produced by the hybridoma hnmc841 which had been prepared by using fusion protein GST-NAIP(841–1052) as the immunogen, belongs to the subclass IgG1 and the epitope thereof is the amino acid sequence of the 841–1052nd region in SEQ ID NO: 1.

Example 2

Production of the Polyclonal Antibody

A rabbit (Japanese White Rabbit) was immunized by the standard method, by using as the immunogen the fusion protein GST-NAIP(256–586) prepared in a manner similar to that of Example 1 (1). The anti-serum was then separated, and the polyclonal antibody was purified by a sepharose 4B column in which the aforementioned fused proteins were bonded.

Example 3

Production of ELISA Kit (1) Primary Antibody-Immobilized Plate

A solution (20 $\mu$g/ml) of the anti-NAIP monoclonal antibody hnmc365 produced in Example 1 was dissolved into 10 mmol/l of potassium phosphate buffer (pH 7.5) containing 150 mmol/l of sodium chloride and 1 g/l of sodium azide. 50 $\mu$l of this solution was pipetted into each hole of a 96-hole plate for ELISA. The plate was stored at 4° C. for 16 hours. Thereafter, the plate was washed with 10 mmol/l potassium phosphate buffer (pH 7.5) containing 150 mmol/l sodium chloride, whereby the plate on which the anti-NAIP monoclonal antibody was immobilized was produced.

(2) Biotinylated Secondary Antibody 0.01 mmol of biotin-amidecaproic acid N-hydroxysuccinic imide ester dissolved into N,N-dimethylformamide was added to 10 mg of the anti-NAIP polyclonal antibody produced in Example 2. The mixture was stored at 25° C. for 3 hours and then subjected to dialysis for 16 hours in 50 mmol/l potassium phosphate buffer (pH 7.4), whereby the biotinylated anti-NAIP polyclonal antibody was produced.

(3) Marker to be Bound to the Secondary Antibody

A solution of horse radish peroxydase-labeled streptoavidin was diluted to the concentration of 0.5 $\mu$g/ml with 10 mmol/l potassium phosphate buffer (pH 7.2) containing 150 mmol/l sodium chloride and 1 g/L casein, whereby the marker solution was obtained.

Example 4

NAIP Assay (1) Method of Operation

Sample solutions containing the purified NAIP at different concentrations were diluted with 10 mmol/l potassium phosphate buffer (pH 7.2) containing 150 mmol/l sodium chloride. 50 $\mu$l of each of the diluted solutions was pipetted into each hole of the plate on which the primary antibodies had been provided in the solid state prepared in Example 3 (1). The plate was stored at 37° C. for 1 hour and then washed off with 10 mmol/l potassium phosphate buffer (pH 7.2) containing 150 mmol/l sodium chloride.

Next, the biotinated anti-NAIP polyclonal antibody of Example 3 (2) was diluted to the concentration of 0.5 $\mu$g/ml with 10 mmol/l potassium phosphate buffer (pH 7.2) containing 150 mmol/l sodium chloride and 1 g/l casein. 100 $\mu$l of each of the diluted solutions was pipetted into each hole of the aforementioned plate. The plate was stored at 37° C. for 1 hour and then washed off with 10 mmol/l potassium phosphate buffer (pH 7.2) containing 150 mmol/l sodium chloride.

As the final step, 100 $\mu$l of the solution of horse radish peroxydase-labeled streptoavidin prepared in Example 3 (3) was pipetted into each hole of the aforementioned plate. The plate was stored at 37° C. for 1 hour and then washed off with 10 mmol/l potassium phosphate buffer (pH 7.2) containing 150 mmol/l sodium chloride.

(2) Color-Developing Reaction and Measurement of Absorbance 3,3',5,5'-tetramethylbenzidine was dissolved into N,N-dimethylformamide so that the concentration of 3,3',5,5'-tetramethylbenzidine was 50 mmol/l. The obtained solution was diluted to 1/100 with 100 mmol/l sodium accetate buffer (pH 5.5) and then filtered by a filtering paper. 0.1 ml of aqueous hydrogen peroxide (10 g/l) was added to 10 ml of the solution, whereby the color developing solution was obtained. 50 $\mu$l of the color developing solution was pipetted into each hole of the aforementioned plate. The plate was stored at 30° C. for 30 minutes. Thereafter, 50 $\mu$l of sulfuric acid (2 mol/l) was pipetted into each hole of the plate, so that the reaction stopped. Absorbance was then measured at 450 nm.

(3) Results

Figure 1:
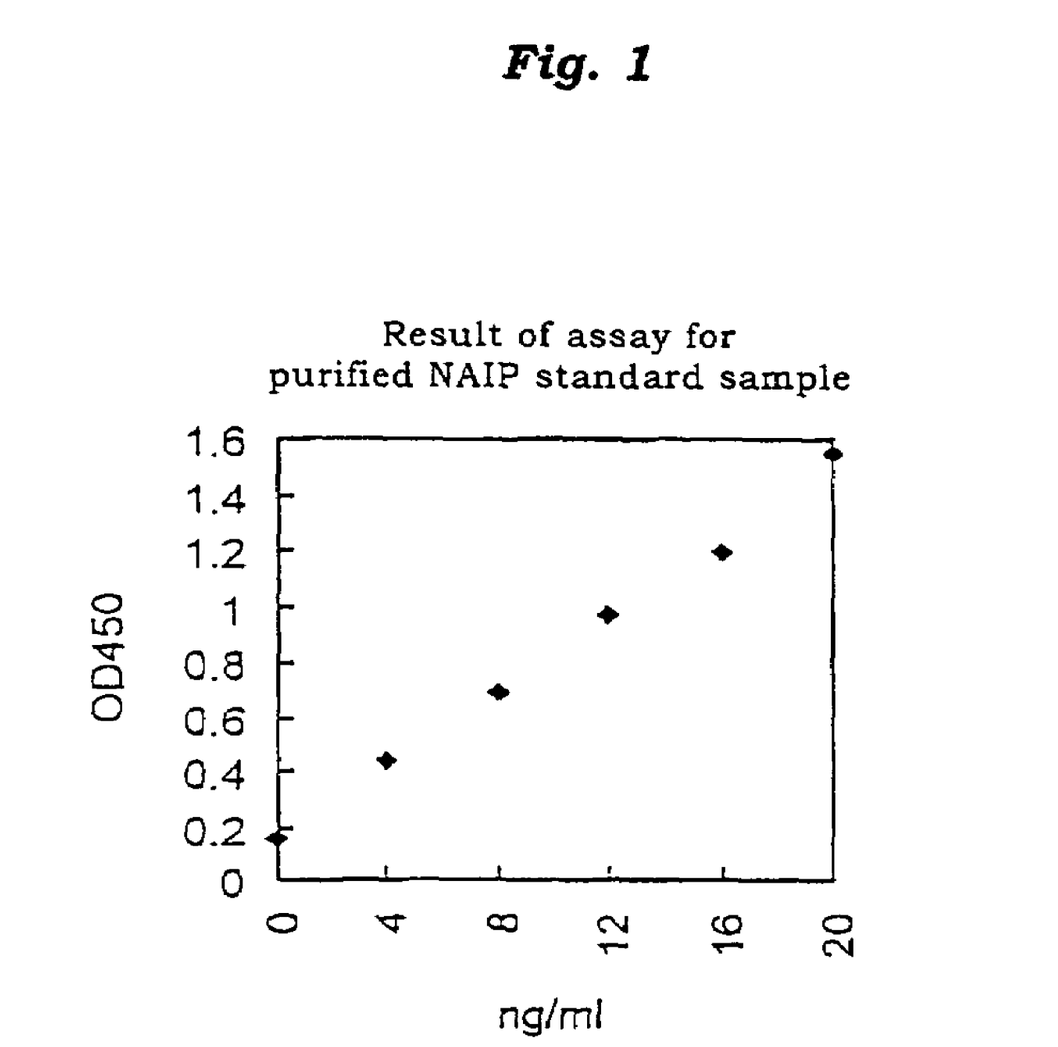
FIG. 1 is a graph that shows a relationship between the concentration of purified NAIP in a sample solution and the absorbance measured by the method described in Examples.

FIG. 1 is a graph that shows the relationship between the concentration of the purified NAIP in the sample solution and the absorbance measured by the aforementioned method. The concentration of NAIP in the sample was measurable because the values thereof resided within the measurable range of 4 ng/ml to 20 ng/ml.

From the results, it was confirmed that, if the NAIP concentration is unknown for a sample, the concentration of NAIP of the sample can be accurately assayed on the basis of the absorbance thereof by utilizing, for example, the measurement results as shown in FIG. 1 as the reference line.

Example 5

Western Blot (1) Preparation of Sample for SDS Gel Electrophoresis

Mononuclear cells were separated from 10 ml of normal human peripheral blood by using Ficoll Paque PLUS (by Amasham-Pharmacia Co.). The obtained mononuclear cells were fixed by 5–10% trichloroacetic acid and then were separated by centrifuging. The separated cells were dissolved into a Tris buffer containing lithium dodesyl sulfate (2%), urea (8M), DTT (1%), and Triton X-100 (1%).

(2) Western Blot

Using the aforementioned sample carried out SDS gel electrophoresis, and the result was transferred to a PVDF film. The PVDF film on which the transfer had been done was treated overnight at 4° C. with TBS containing skimmed milk (10%) and Tween 20 (0.05%). The PVDF film was then washed with TBS (TBST) containing Tween 20 (0.05%). Each antibody was diluted with TBST in an appropriate manner and allowed to react at the room temperature for 2 hours. Then, after washing with TBST, peroxydase-labeled anti-rabbit Ig antibody or anti-mouse Ig antibody (by Amasham-Pharmacia Co.) was added for reaction that proceeded at the room temperature for 1 hour. After washing with TBST, the treatment with the ECL PLUS reagent (by Amasham-Pharmacia Co.) and exposure onto an X-ray film followed, whereby signals were obtained.

(3) Results

Figure 2:
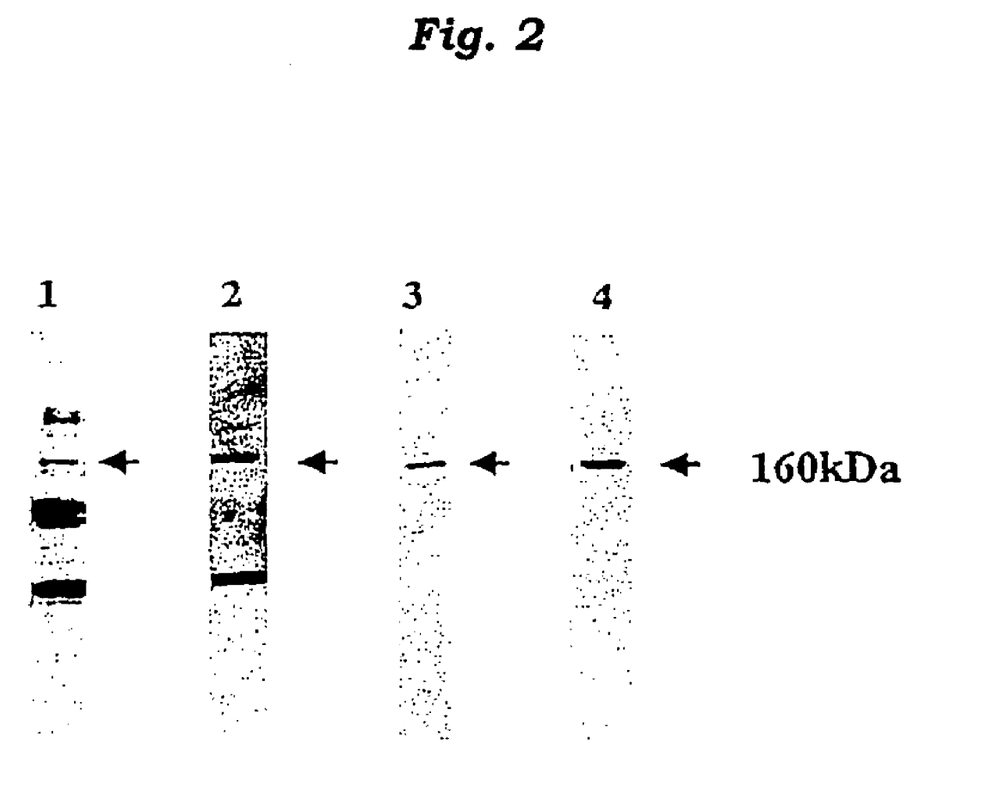
FIG. 2 shows the results of Western Blotting in which anti-NAIP antibodies of a mononuclear cell solution derived from human peripheral blood were used. Lanes represent, in order, 1. monoclonal antibody hnmc365; 2. monoclonal antibody hnmc381; 3. monoclonal antibody hnmc841; and 4. polyclonal antibody. The concentrations of the antibodies each resulted from dilution by 250 times.

The results are shown in FIG. 2. In all of the three types of blots in which the monoclonal antibodies were used, signals of 160 kDa which had been observed for the anti-NAIP polyclonal antibody were detected.

From the aforementioned results, it was confirmed that the monoclonal antibodies hnmc365, hnmc381 and hnmc841 prepared in Example 1 are monoclonal antibodies that specifically recognize NAIP and thus detection of NAIP is possible by using these monoclonal antibodies.

INDUSTRIAL APPLICABILITY

As described above in detail, the invention of the present application allows simple but accurate assay of human apoptosis inhibitory protein (NAIP) present in a sample isolated from an organism. The present invention will facilitate better understanding of the mechanism of patients developing symptoms of various apoptosis-related diseases, better diagnosis of the danger of developing the diseases, prevention of the development of the diseases or reduction of the severity of the diseases, and development of the medical technique and medicines for treatment.

---

What is claimed is:

1. An anti-NAIP monoclonal antibody hnmc365, which is produced from hybridoma 656-1 (FERM BP-6919), and has an epitope at the 354–365th region in SEQ ID NO: 1.

2. An anti-NAIP monoclonal antibody hnmc381, which is produced from hybridoma 656-2 (FERM BP-6920), and has an epitope at the 373–387th region in SEQ ID NO: 1.

3. An anti-NAIP monoclonal antibody hnmc841, which is produced from hybridoma 841 (FERM BP-6921), and has an epitope at the 841–1052nd region in SEQ ID NO: 1.

4. A NAIP assay kit comprising:
   (a) a plate on which an anti-NAIP primary antibody is immobilized; and
   (b) an anti-NAIP secondary antibody labeled with a marker, wherein;
   (1) the primary antibody and the secondary antibody are both the anti-NAIP monoclonal antibody of any one of the monoclonal antibodies of claims 1–3, wherein:
      (i) the primary antibody recognizes the amino acid sequence of the 256–585th amino acids of SEQ ID NO: 1 and the secondary antibody recognizes the amino acid sequence of the 841–1052nd amino acids of SEQ ID NO: 1; or
      (ii) the primary antibody recognizes the amino acid sequence of the 841–1052nd amino acids of SEQ ID NO: 1 and the secondary antibody recognizes the amino acid sequence of the 256–585th amino acids of SEQ ID NO: 1; or
   (2) the primary antibody is the anti-NAIP monoclonal antibody of any one of the monoclonal antibodies of claims 2–3 which recognizes the amino acid sequence of the 256–585th amino acids or the 841–1052nd amino acids of SEQ ID NO: 1 and the secondary antibody is an anti-NAIP polyclonal antibody; or
   (3) the primary antibody is an anti-NAIP polyclonal antibody and the secondary antibody is the anti-NAIP monoclonal antibody of any one of the monoclonal antibodies of claims 2–3 which recognizes the amino acid sequence of the 256–585th amino acids or the 841–1052nd amino acids of SEQ ID NO: 1.

5. The NAIP assay kit of claim 4, wherein the marker is a radioactive isotope or a fluorescent colorant.

6. The NAIP assay kit of claim of claim 4, wherein the marker is an enzyme and the kit further includes a substrate which develops a color by the enzyme activity.

7. A NAIP assay kit comprising:
(a) a plate on which an anti-NAIP primary antibody is immobilized;
(b) an anti-NAIP secondary antibody; and
(c) a marker to be bound with the secondary antibody, wherein:
(1) the primary antibody and the secondary antibody are both the anti-NAIP monoclonal antibody of any one of the monoclonal antibodies of claims 1–3, wherein:
  (i) the primary antibody recognizes the amino acid sequence of the 256–585th amino acids of SEQ ID NO: 1 and the secondary antibody recognizes the amino acid sequence of the 841–1052nd amino acids of SEQ ID NO: 1; or
  (ii) the primary antibody recognizes the amino acid sequence of the 841–1052nd amino acids of SEQ ID NO: 1 and the secondary antibody recognizes the amino acid sequence of the 256–585th amino acids of SEQ ID NO: 1; or
(2) the primary antibody is the anti-NAIP monoclonal antibody of any one of the monoclonal antibodies of claims 2–3 which recognizes the amino acid sequence of the 256–585th amino acids or the 841–1052nd amino acids of SEQ ID NO: 1 and the secondary antibody is an anti-NAIP polyclonal antibody; or
(3) the primary antibody is an anti-NAIP polyclonal antibody and the secondary antibody is the anti-NAIP monoclonal antibody of any one of the monoclonal antibodies of claims 2–3 which recognizes the amino acid sequence of the 256–585th amino acids or the 841–1052nd amino acids of SEQ ID NO: 1.

8. The NAIP assay kit of claim 7, wherein the marker is a radioactive isotope or a fluorescent colorant.

9. The NAIP assay kit of claim of claim 7, wherein the marker is an enzyme and the kit further includes a substrate which develops a color by the enzyme activity.

* * * * *

UNITED STATES PATENT AND TRADEMARK OFFICE
CERTIFICATE OF CORRECTION

PATENT NO. : 6,982,322 B1 Page 1 of 1
APPLICATION NO. : 09/830338
DATED : January 3, 2006
INVENTOR(S) : Johe Ikeda et al.

It is certified that error appears in the above-identified patent and that said Letters Patent is hereby corrected as shown below:

In column 24, line 58, please replace "claims 2-3" with --claims 1-3-- after "of" and before "which".

In column 24, line 65, please replace "claims 2-3" with --claims 1-3-- after "of" and before "which".

In column 26, line 5, please replace "claims 2-3" with --claims 1-3-- after "of" and before "which".

In column 26, line 12, please replace "claims 2-3" with --claims 1-3-- after "of" and before "which".

Signed and Sealed this

Twentieth Day of November, 2007

JON W. DUDAS
*Director of the United States Patent and Trademark Office*

SEQUENCE LISTING

<160> NUMBER OF SEQ ID NOS: 2

<210> SEQ ID NO 1
<211> LENGTH: 1403
<212> TYPE: PRT
<213> ORGANISM: Homo sapiens

<400> SEQUENCE: 1

```
Met Ala Thr Gln Gln Lys Ala Ser Asp Glu Arg Ile Ser Gln Phe Asp
 1               5                  10                  15

His Asn Leu Leu Pro Glu Leu Ser Ala Leu Leu Gly Leu Asp Ala Val
            20                  25                  30

Gln Leu Ala Lys Glu Leu Glu Glu Glu Gln Lys Glu Arg Ala Lys
        35                  40                  45

Met Gln Lys Gly Tyr Asn Ser Gln Met Arg Ser Glu Ala Lys Arg Leu
    50                  55                  60

Lys Thr Phe Val Thr Tyr Glu Pro Tyr Ser Ser Trp Ile Pro Gln Glu
65                  70                  75                  80

Met Ala Ala Ala Gly Phe Tyr Phe Thr Gly Val Lys Ser Gly Ile Gln
                85                  90                  95

Cys Phe Cys Cys Ser Leu Ile Leu Phe Gly Ala Gly Leu Thr Arg Leu
            100                 105                 110

Pro Ile Glu Asp His Lys Arg Phe His Pro Asp Cys Gly Phe Leu Leu
        115                 120                 125

Asn Lys Asp Val Gly Asn Ile Ala Lys Tyr Asp Ile Arg Val Lys Asn
    130                 135                 140
```

-continued

```
Leu Lys Ser Arg Leu Arg Gly Gly Lys Met Arg Tyr Gln Glu Glu Glu
145                 150                 155                 160

Ala Arg Leu Ala Ser Phe Arg Asn Trp Pro Phe Tyr Val Gln Gly Ile
                165                 170                 175

Ser Pro Cys Val Leu Ser Glu Ala Gly Phe Val Phe Thr Gly Lys Gln
            180                 185                 190

Asp Thr Val Gln Cys Phe Ser Cys Gly Gly Cys Leu Gly Asn Trp Glu
        195                 200                 205

Glu Gly Asp Asp Pro Trp Lys Glu His Ala Lys Trp Phe Pro Lys Cys
    210                 215                 220

Glu Phe Leu Arg Ser Lys Lys Ser Ser Glu Glu Ile Thr Gln Tyr Ile
225                 230                 235                 240

Gln Ser Tyr Lys Gly Phe Val Asp Ile Thr Gly Glu His Phe Val Asn
                245                 250                 255

Ser Trp Val Gln Arg Glu Leu Pro Met Ala Ser Ala Tyr Cys Asn Asp
            260                 265                 270

Ser Ile Phe Ala Tyr Glu Glu Leu Arg Leu Asp Ser Phe Lys Asp Trp
        275                 280                 285

Pro Arg Glu Ser Ala Val Gly Val Ala Ala Leu Ala Lys Ala Gly Leu
    290                 295                 300

Phe Tyr Thr Gly Ile Lys Asp Ile Val Gln Cys Phe Ser Cys Gly Gly
305                 310                 315                 320

Cys Leu Glu Lys Trp Gln Glu Gly Asp Asp Pro Leu Asp Asp His Thr
                325                 330                 335

Arg Cys Phe Pro Asn Cys Pro Phe Leu Gln Asn Met Lys Ser Ser Ala
            340                 345                 350

Glu Val Thr Pro Asp Leu Gln Ser Arg Gly Glu Leu Cys Glu Leu Leu
        355                 360                 365

Glu Thr Thr Ser Glu Ser Asn Leu Glu Asp Ser Ile Ala Val Gly Pro
    370                 375                 380

Ile Val Pro Glu Met Ala Gln Gly Glu Ala Gln Trp Phe Gln Glu Ala
385                 390                 395                 400

Lys Asn Leu Asn Glu Gln Leu Arg Ala Ala Tyr Thr Ser Ala Ser Phe
                405                 410                 415

Arg His Met Ser Leu Leu Asp Ile Ser Ser Asp Leu Ala Thr Asp His
            420                 425                 430

Leu Leu Gly Cys Asp Leu Ser Ile Ala Ser Lys His Ile Ser Lys Pro
        435                 440                 445

Val Gln Glu Pro Leu Val Leu Pro Glu Val Phe Gly Asn Leu Asn Ser
    450                 455                 460

Val Met Cys Val Glu Gly Glu Ala Gly Ser Gly Lys Thr Val Leu Leu
465                 470                 475                 480

Lys Lys Ile Ala Phe Leu Trp Ala Ser Gly Cys Cys Pro Leu Leu Asn
                485                 490                 495

Arg Phe Gln Leu Val Phe Tyr Leu Ser Leu Ser Ser Thr Arg Pro Asp
            500                 505                 510

Glu Gly Leu Ala Ser Ile Ile Cys Asp Gln Leu Leu Glu Lys Glu Gly
        515                 520                 525

Ser Val Thr Glu Met Cys Met Arg Asn Ile Ile Gln Gln Leu Lys Asn
    530                 535                 540

Gln Val Leu Phe Leu Leu Asp Asp Tyr Lys Glu Ile Cys Ser Ile Pro
545                 550                 555                 560

Gln Val Ile Gly Lys Leu Ile Gln Lys Asn His Leu Ser Arg Thr Cys
```

-continued

```
                565                 570                 575
Leu Leu Ile Ala Val Arg Thr Asn Arg Ala Arg Asp Ile Arg Arg Tyr
            580                 585                 590
Leu Glu Thr Ile Leu Glu Ile Lys Ala Phe Pro Phe Tyr Asn Thr Val
            595                 600                 605
Cys Ile Leu Arg Lys Leu Phe Ser His Asn Met Thr Arg Leu Arg Lys
            610                 615                 620
Phe Met Val Tyr Phe Gly Lys Asn Gln Ser Leu Gln Lys Ile Gln Lys
625                 630                 635                 640
Thr Pro Leu Phe Val Ala Ala Ile Cys Ala His Trp Phe Gln Tyr Pro
            645                 650                 655
Phe Asp Pro Ser Phe Asp Val Ala Val Phe Lys Ser Tyr Met Glu
            660                 665                 670
Arg Leu Ser Leu Arg Asn Lys Ala Thr Ala Glu Ile Leu Lys Ala Thr
            675                 680                 685
Val Ser Ser Cys Gly Glu Leu Ala Leu Lys Gly Phe Phe Ser Cys Cys
            690                 695                 700
Phe Glu Phe Asn Asp Asp Asp Leu Ala Glu Ala Gly Val Asp Glu Asp
705                 710                 715                 720
Glu Asp Leu Thr Met Cys Leu Met Ser Lys Phe Thr Ala Gln Arg Leu
            725                 730                 735
Arg Pro Phe Tyr Arg Phe Leu Ser Pro Ala Phe Gln Glu Phe Leu Ala
            740                 745                 750
Gly Met Arg Leu Ile Glu Leu Leu Asp Ser Asp Arg Gln Glu His Gln
            755                 760                 765
Asp Leu Gly Leu Tyr His Leu Lys Gln Ile Asn Ser Pro Met Met Thr
            770                 775                 780
Val Ser Ala Tyr Asn Asn Phe Leu Asn Tyr Val Ser Ser Leu Pro Ser
785                 790                 795                 800
Thr Lys Ala Gly Pro Lys Ile Val Ser His Leu Leu His Leu Val Asp
            805                 810                 815
Asn Lys Glu Ser Leu Glu Asn Ile Ser Glu Asn Asp Asp Tyr Leu Lys
            820                 825                 830
His Gln Pro Glu Ile Ser Leu Gln Met Gln Leu Leu Arg Gly Leu Trp
            835                 840                 845
Gln Ile Cys Pro Gln Ala Tyr Phe Ser Met Val Ser Glu His Leu Leu
            850                 855                 860
Val Leu Ala Leu Lys Thr Ala Tyr Gln Ser Asn Thr Val Ala Ala Cys
865                 870                 875                 880
Ser Pro Phe Val Leu Gln Phe Leu Gln Gly Arg Thr Leu Thr Leu Gly
            885                 890                 895
Ala Leu Asn Leu Gln Tyr Phe Phe Asp His Pro Glu Ser Leu Ser Leu
            900                 905                 910
Leu Arg Ser Ile His Phe Pro Ile Arg Gly Asn Lys Thr Ser Pro Arg
            915                 920                 925
Ala His Phe Ser Val Leu Glu Thr Cys Phe Asp Lys Ser Gln Val Pro
            930                 935                 940
Thr Ile Asp Gln Asp Tyr Ala Ser Ala Phe Glu Pro Met Asn Glu Trp
945                 950                 955                 960
Glu Arg Asn Leu Ala Glu Lys Glu Asp Asn Val Lys Ser Tyr Met Asp
            965                 970                 975
Met Gln Arg Arg Ala Ser Pro Asp Leu Ser Thr Gly Tyr Trp Lys Leu
            980                 985                 990
```

```
Ser Pro Lys Gln Tyr Lys Ile Pro Cys Leu Glu Val Asp Val Asn Asp
        995                 1000                1005

Ile Asp Val Val Gly Gln Asp Met Leu Glu Ile Leu Met Thr Val Phe
    1010                1015                1020

Ser Ala Ser Gln Arg Ile Glu Leu His Leu Asn His Ser Arg Gly Phe
1025                1030                1035                1040

Ile Glu Ser Ile Arg Pro Ala Leu Glu Leu Ser Lys Ala Ser Val Thr
                1045                1050                1055

Lys Cys Ser Ile Ser Lys Leu Glu Leu Ser Ala Ala Glu Gln Glu Leu
            1060                1065                1070

Leu Leu Thr Leu Pro Ser Leu Glu Ser Leu Glu Val Ser Gly Thr Ile
        1075                1080                1085

Gln Ser Gln Asp Gln Ile Phe Pro Asn Leu Asp Lys Phe Leu Cys Leu
    1090                1095                1100

Lys Glu Leu Ser Val Asp Leu Glu Gly Asn Ile Asn Val Phe Ser Val
1105                1110                1115                1120

Ile Pro Glu Glu Phe Pro Asn Phe His His Met Glu Lys Leu Leu Ile
                1125                1130                1135

Gln Ile Ser Ala Glu Tyr Asp Pro Ser Lys Leu Val Lys Leu Ile Gln
            1140                1145                1150

Asn Ser Pro Asn Leu His Val Phe His Leu Lys Cys Asn Phe Phe Ser
        1155                1160                1165

Asp Phe Gly Ser Leu Met Thr Met Leu Val Ser Cys Lys Lys Leu Thr
    1170                1175                1180

Glu Ile Lys Phe Ser Asp Ser Phe Phe Gln Ala Val Pro Phe Val Ala
1185                1190                1195                1200

Ser Leu Pro Asn Phe Ile Ser Leu Lys Ile Leu Asn Leu Glu Gly Gln
                1205                1210                1215

Gln Phe Pro Asp Glu Thr Ser Glu Lys Phe Ala Tyr Ile Leu Gly
            1220                1225                1230

Ser Leu Ser Asn Leu Glu Glu Leu Ile Leu Pro Thr Gly Asp Gly Ile
        1235                1240                1245

Tyr Arg Val Ala Lys Leu Ile Ile Gln Gln Cys Gln Gln Leu His Cys
    1250                1255                1260

Leu Arg Val Leu Ser Phe Phe Lys Thr Leu Asn Asp Asp Ser Val Val
1265                1270                1275                1280

Glu Ile Ala Lys Val Ala Ile Ser Gly Gly Phe Gln Lys Leu Glu Asn
                1285                1290                1295

Leu Lys Leu Ser Ile Asn His Lys Ile Thr Glu Glu Gly Tyr Arg Asn
        1300                1305                1310

Phe Phe Gln Ala Leu Asp Asn Met Pro Asn Leu Gln Glu Leu Asp Ile
    1315                1320                1325

Ser Arg His Phe Thr Glu Cys Ile Lys Ala Gln Ala Thr Thr Val Lys
        1330                1335                1340

Ser Leu Ser Gln Cys Val Leu Arg Leu Pro Arg Leu Ile Arg Leu Asn
1345                1350                1355                1360

Met Leu Ser Trp Leu Leu Asp Ala Asp Asp Ile Ala Leu Leu Asn Val
                1365                1370                1375

Met Lys Glu Arg His Pro Gln Ser Lys Tyr Leu Thr Ile Leu Gln Lys
            1380                1385                1390

Trp Ile Leu Pro Phe Ser Pro Ile Ile Gln Lys
    1395                1400        1403
```

<210> SEQ ID NO 2
<211> LENGTH: 5984
<212> TYPE: DNA
<213> ORGANISM: Homo sapiens
<220> FEATURE:
<221> NAME/KEY: CDC
<222> LOCATION: (292)..(4500)

<400> SEQUENCE: 2

| | | | | | |
|---|---|---|---|---|---|
| acaaaaggtc | ctgtgctcac | ctgggaccct | tctggacgtt | gccctgtgtt | cctcttcgcc | 60 |
| tgcctgttca | tctacgacga | accccgggta | ttgaccccag | acaacaatgc | cacttcatat | 120 |
| tggggacttc | gtctgggatt | ccaaggtgca | ttcattgcaa | agttccttaa | atattttctc | 180 |
| actgcttcct | actaaaggac | ggacagagca | tttgttcttc | agccacatac | tttccttcca | 240 |
| ctggccagca | ttctcctcta | ttagactaga | actgtggata | aacctcagaa | aatggccacc | 300 |
| cagcagaaag | cctctgacga | gaggatctcc | cagtttgatc | acaatttgct | gccagagctg | 360 |
| tctgctcttc | tgggcctaga | tgcagttcag | ttggcaaagg | aactagaaga | agaggagcag | 420 |
| aaggagcgag | caaaaatgca | gaaaggctac | aactctcaaa | tgcgcagtga | agcaaaaagg | 480 |
| ttaaagactt | ttgtgactta | tgagccgtac | agctcatgga | taccacagga | gatggcggcc | 540 |
| gctgggtttt | acttcactgg | ggtaaaatct | gggattcagt | gcttctgctg | tagcctaatc | 600 |
| ctctttggtg | ccggcctcac | gagactcccc | atagaagacc | acaagaggtt | tcatccagat | 660 |
| tgtgggttcc | ttttgaacaa | ggatgttggt | aacattgcca | agtacgacat | aagggtgaag | 720 |
| aatctgaaga | gcaggctgag | aggaggtaaa | atgaggtacc | aagaagagga | ggctagactt | 780 |
| gcatccttca | ggaactggcc | attttatgtc | caagggatat | ccccttgtgt | gctctcagag | 840 |
| gctggctttg | tctttacagg | taaacaggac | acggtacagt | gttttttcctg | tggtggatgt | 900 |
| ttaggaaatt | gggaagaagg | agatgatcct | tggaaggaac | atgccaaatg | gttccccaaa | 960 |
| tgtgaatttc | ttcggagtaa | gaaatcctca | gaggaaatta | cccagtatat | tcaaagctac | 1020 |
| aagggatttg | ttgacataac | gggagaacat | tttgtgaatt | cctgggtcca | gagagaatta | 1080 |
| cctatggcat | cagcttattg | caatgacagc | atctttgctt | acgaagaact | acggctggac | 1140 |
| tcttttaagg | actggccccg | ggaatcagct | gtgggagttg | cagcactggc | caaagcaggt | 1200 |
| cttttctaca | caggtataaa | ggacatcgtc | cagtgctttt | cctgtggagg | gtgtttagag | 1260 |
| aaatggcagg | aaggtgatga | cccattagac | gatcacacca | gatgttttcc | caattgtcca | 1320 |
| tttctccaaa | atatgaagtc | ctctgcggaa | gtgactccag | accttcagag | ccgtggtgaa | 1380 |
| ctttgtgaat | tactggaaac | cacaagtgaa | agcaatcttg | aagattcaat | agcagttggt | 1440 |
| cctatagtgc | cagaaatggc | acagggtgaa | gcccagtggt | tcaagaggc | aaagaatctg | 1500 |
| aatgagcagc | tgagagcagc | ttataccagc | gccagtttcc | gccacatgtc | tttgcttgat | 1560 |
| atctcttccg | atctggccac | ggaccacttg | ctgggctgtg | atctgtctat | tgcttcaaaa | 1620 |
| cacatcagca | aacctgtgca | agaacctctg | gtgctgcctg | aggtctttgg | caacttgaac | 1680 |
| tctgtcatgt | gtgtggaggg | tgaagctgga | agtggaaaga | cggtcctcct | gaagaaaata | 1740 |
| gcttttctgt | gggcatctgg | atgctgtccc | ctgttaaaca | ggttccagct | ggttttctac | 1800 |
| ctctcccctta | gttccaccag | accagacgag | gggctggcca | gtatcatctg | tgaccagctc | 1860 |
| ctagagaaag | aaggatctgt | tactgaaatg | tgcatgagga | acattatcca | gcagttaaag | 1920 |
| aatcaggtct | tattccttttt | agatgactac | aaagaaatat | gttcaatccc | tcaagtcata | 1980 |
| ggaaaactga | ttcaaaaaaa | ccacttatcc | cggacctgcc | tattgattgc | tgtccgtaca | 2040 |

-continued

```
aacagggcca gggacatccg ccgatacccta gagaccattc tagagatcaa agcatttccc    2100
ttttataata ctgtctgtat attacggaag ctcttttcac ataatatgac tcgtctgcga    2160
aagtttatgg tttactttgg aaagaaccaa agtttgcaga agatacagaa aactcctctc    2220
tttgtggcgg cgatctgtgc tcattggttt cagtatcctt ttgacccatc ctttgatgat    2280
gtggctgttt tcaagtccta tatggaacgc cttccttaa ggaacaaagc gacagctgaa    2340
attctcaaag caactgtgtc ctcctgtggt gagctggcct tgaaagggtt tttttcatgt    2400
tgctttgagt ttaatgatga tgatctcgca gaagcagggg ttgatgaaga tgaagatcta    2460
accatgtgct tgatgagcaa atttacagcc cagagactaa gaccattcta ccggtttta    2520
agtcctgcct tccaagaatt tcttgcgggg atgaggctga ttgaactcct ggattcagat    2580
aggcaggaac atcaagattt gggactgtat catttgaaac aaatcaactc acccatgatg    2640
actgtaagcg cctacaacaa ttttttgaac tatgtctcca gcctcccttc aacaaaagca    2700
gggcccaaaa ttgtgtctca tttgctccat ttagtggata caaagagtc attggagaat    2760
atatctgaaa atgatgacta cttaaagcac cagccagaaa tttcactgca gatgcagtta    2820
cttaggggat tgtggcaaat ttgtccacaa gcttactttt caatggtttc agaacattta    2880
ctggttcttg ccctgaaaac tgcttatcaa agcaacactg ttgctgcgtg ttctccattt    2940
gttttgcaat tccttcaagg gagaaacactg actttgggtg cgcttaactt acagtacttt    3000
ttcgaccacc cagaaagctt gtcattgttg aggagcatcc acttcccaat acgaggaaat    3060
aagacatcac ccagagcaca tttttcagtt ctggaaacat gttttgacaa atcacagtg    3120
ccaactatag atcaggacta tgcttctgcc tttgaaccta tgaatgaatg ggagcgaaat    3180
ttagctgaaa aagaggataa tgtaaagagc tatatggata tgcagcgcag ggcatcacca    3240
gaccttagta ctggctattg gaaactttct ccaaagcagt acaagattcc ctgtctagaa    3300
gtcgatgtga atgatattga tgttgtaggc caggatatgc ttgagattct aatgacagtt    3360
ttctcagctt cacagcgcat cgaactccat ttaaaccaca gcagaggctt tatagaaagc    3420
atccgcccag ctcttgagct gtctaaggcc tctgtcacca agtgctccat aagcaagttg    3480
gaactcagcg cagccgaaca ggaactgctt ctcaccctgc cttccctgga atctcttgaa    3540
gtctcaggga caatccagtc acaagaccaa atctttccta atctggataa gttcctgtgc    3600
ctgaaagaac tgtctgtgga tctggagggc aatataaatg ttttttcagt cattcctgaa    3660
gaatttccaa acttccacca tatggagaaa ttattgatcc aaatttcagc tgagtatgat    3720
ccttccaaac tagtaaaatt aattcaaaat tctccaaacc ttcatgtttt ccatctgaag    3780
tgtaacttct tttcggattt tgggtctctc atgactatgc ttgtttcctg taagaaactc    3840
acagaaatta agttttcgga ttcatttttt caagccgtcc catttgttgc cagtttgcca    3900
aattttattt ctctgaagat attaaatctt gaaggccagc aatttcctga tgaggaaaca    3960
tcagaaaaat ttgcctacat tttaggttct cttagtaacc tggaagaatt gatccttcct    4020
actggggatg gaatttatcg agtggccaaa ctgatcatcc agcagtgtca gcagcttcat    4080
tgtctccgag tcctctcatt tttcaagact ttgaatgatg acagcgtggt ggaaattgcc    4140
aaagtagcaa tcagtggagg tttccagaaa cttgagaacc taaagctttc aatcaatcac    4200
aagattacag aggaaggata cagaaatttc tttcaagcac tggacaacat gccaaacttg    4260
caggagttgg acatctccag gcatttcaca gagtgtatca agctcaggc cacaacagtc    4320
aagtctttga gtcaatgtgt gttacgacta ccaaggctca ttagactgaa catgttaagt    4380
tggctcttgg atgcagatga tattgcattg cttaatgtca tgaaagaaag acatcctcaa    4440
```

```
tctaagtact taactattct ccagaaatgg atactgccgt tctctccaat cattcagaaa    4500
taaaagattc agctaaaaac tgctgaatca ataatttgtc ttggggcata ttgaggatgt    4560
aaaaaaagtt gttgattaat gctaaaaacc aaattatcca aaattatttt attaaatatt    4620
gcatacaaaa gaaaatgtgt aaggcttgct aaaaaacaaa acaaaacaaa acacagtcct    4680
gcatactcac caccaagctc aagaaataaa tcatcaccaa tacctttgag gtccctgagt    4740
aatccacccc agctaaaggc aaacccttca atcaagttta tacagcaaac cctccattgt    4800
ccatggtcaa cagggaaggg gttggggaca ggtctgccaa tctatctaaa agccacaata    4860
tggaagaagt attcaattta tataataaat ggctaactta acggttgaat cactttcata    4920
catggatgaa acgggtttaa cacaggatcc acatgaatct tctgtgggcc aaaatatgtt    4980
ccttaatcct tgtagaacct gtcttctata ttgaactagc tttggtacag tagagttaac    5040
ttactttcca tttatccact gccaatataa agaggaaaca ggggttaggg aaaaatgact    5100
tcattccaga ggcttctcag agttcaacat atgctataat ttagaatttt cttatgaatc    5160
cactctactt gggtagaaaa tattttatct ctagtgattg catattattt ccatatcata    5220
gtatttcata gtattatatt tgatatgagt gtctatatca atgtcagtgt ccagaatttc    5280
gttcctacca gttgagtagt tttctgaacg gccagaagac cattcgaaat tcatgatact    5340
actataagtt ggtaaacaac catactttta tcctcatttt tattctcact aagaaaaaag    5400
tcaactcccc tccccttgcc caagtatgaa atatagggac agtatgtatg gtgtggtctc    5460
atttgtttag aaaaccactt atgactgggt gcggtggctc acacctgtaa tcccagcact    5520
ttgggaggct gaggcgggcg aatcatttga ggtgaggagt tcgagaccgg cctggccagc    5580
atggtgaaac cccatttttg ctaaaggtac aaaaattagc caggtgtggt ggcacatgcc    5640
tgtggtccca gccactgggg cggctgagac gcaggacttg cttgaacccg ggaggcagag    5700
gttgcagtga gccgagatgg cgccactgca ttccagcctg ggcaacagag caagaccctg    5760
tctgtttcaa aacaaaaaac aaaaccactt atattgctag ctacattaag aatttctgaa    5820
tatgttactg agcttgcttg tggtaaccat ttataatatc agaaagtata tgtacaccaa    5880
aacatgttga acatccatgt tgtacaactg aaatataaat aattttgtca attataccta    5940
aataaaactg gaaaaaaaaa aaaaaaaaa aaaaaaaaa aaaa                      5984
```